(12) United States Patent
McClintock

(10) Patent No.: US 9,498,261 B2
(45) Date of Patent: Nov. 22, 2016

(54) LAMINAR HOOK INSERTION DEVICE

(71) Applicant: K2M, Inc., Leesburg, VA (US)

(72) Inventor: Larry McClintock, Gore, VA (US)

(73) Assignee: K2M, INC., Leesburg, VA (US)

(*) Notice: Subject to any disclaimer, the term of this patent is extended or adjusted under 35 U.S.C. 154(b) by 0 days.

(21) Appl. No.: 15/010,040

(22) Filed: Jan. 29, 2016

(65) Prior Publication Data

US 2016/0143673 A1    May 26, 2016

Related U.S. Application Data

(62) Division of application No. 13/209,542, filed on Aug. 15, 2011, now Pat. No. 9,247,962.

(51) Int. Cl.
| | | |
|---|---|---|
| *A61B 17/70* | (2006.01) | |
| *A61B 17/56* | (2006.01) | |
| *A61B 17/80* | (2006.01) | |

(52) U.S. Cl.
CPC ......... *A61B 17/7076* (2013.01); *A61B 17/56* (2013.01); *A61B 17/7044* (2013.01); *A61B 17/7032* (2013.01); *A61B 17/808* (2013.01); *A61B 2017/564* (2013.01)

(58) Field of Classification Search
USPC .................................................. 606/99, 330
See application file for complete search history.

(56) References Cited

U.S. PATENT DOCUMENTS

| | | | |
|---|---|---|---|
| 4,409,968 A * | 10/1983 | Drummond | A61B 17/7002 606/276 |
| 5,005,562 A | 4/1991 | Cotrel | |
| 5,102,412 A * | 4/1992 | Rogozinski | A61B 17/7082 606/250 |
| 5,257,993 A | 11/1993 | Asher et al. | |
| 5,263,954 A | 11/1993 | Schlapfer et al. | |
| 5,346,493 A | 9/1994 | Stahurski et al. | |
| 5,368,594 A | 11/1994 | Martin et al. | |
| 5,374,267 A | 12/1994 | Siegal | |
| 5,397,363 A | 3/1995 | Gelbard | |
| 5,415,659 A | 5/1995 | Lee et al. | |
| 5,437,669 A | 8/1995 | Yuan et al. | |
| 5,476,464 A | 12/1995 | Metz-Stavenhagen et al. | |
| 5,527,314 A | 6/1996 | Brumfield et al. | |
| 5,542,946 A | 8/1996 | Logroscino et al. | |
| 5,575,792 A | 11/1996 | Errico et al. | |
| 5,578,033 A | 11/1996 | Errico et al. | |
| 5,584,832 A | 12/1996 | Schlapfer | |

(Continued)

FOREIGN PATENT DOCUMENTS

| | | | | |
|---|---|---|---|---|
| WO | 2009/091689 | 7/2009 | | |
| WO | WO 2009091689 A1 * | 7/2009 | ......... | A61B 17/7044 |

*Primary Examiner* — Jan Christopher Merene
(74) *Attorney, Agent, or Firm* — Carter, DeLuca, Farrell & Schmidt, LLP

(57) ABSTRACT

A surgical hook insertion device includes an elongate body defining a lumen therethrough and an actuation assembly. The elongate body has a retaining portion configured and dimensioned to releasably retain a laminar hook therein. The actuation assembly includes an actuation rod and an actuator member. The actuation rod is slidably disposed within the lumen of the elongate body. The actuator member is operatively coupled with the actuation rod and is slidably mounted on the elongate body, wherein the actuation assembly is transitionable between a first position in which a portion of the actuation rod engages the laminar hook releasably disposed in the retaining portion and a second position in which the actuation rod disengages the laminar hook.

15 Claims, 10 Drawing Sheets

(56) References Cited

U.S. PATENT DOCUMENTS

| | | | |
|---|---|---|---|
| 5,609,592 A | 3/1997 | Brumfield et al. | |
| 5,609,593 A | 3/1997 | Errico et al. | |
| 5,609,594 A | 3/1997 | Errico et al. | |
| 5,620,444 A | 4/1997 | Assaker | |
| 5,630,816 A | 5/1997 | Kambin | |
| 5,630,817 A | 5/1997 | Rokegem et al. | |
| 5,676,665 A | 10/1997 | Bryan | |
| 5,688,273 A | 11/1997 | Errico et al. | |
| 5,688,274 A | 11/1997 | Errico et al. | |
| 5,725,527 A | 3/1998 | Biedermann et al. | |
| 5,733,285 A | 3/1998 | Errico et al. | |
| 5,741,254 A | 4/1998 | Henry et al. | |
| 5,752,957 A | 5/1998 | Ralph et al. | |
| 5,810,816 A | 9/1998 | Roussouly et al. | |
| 5,810,817 A | 9/1998 | Roussouly et al. | |
| 5,810,818 A | 9/1998 | Errico et al. | |
| 5,888,221 A | 3/1999 | Gelbard | |
| 5,928,232 A | 7/1999 | Howland et al. | |
| 5,989,250 A | 11/1999 | Wagner et al. | |
| 6,010,503 A | 1/2000 | Richelsoph et al. | |
| 6,077,263 A | 6/2000 | Ameil et al. | |
| 6,086,588 A | 7/2000 | Ameil et al. | |
| 6,132,430 A | 10/2000 | Wagner | |
| 6,322,562 B1 | 11/2001 | Wolter | |
| 6,352,537 B1 | 3/2002 | Strnad | |
| 6,416,515 B1 | 7/2002 | Wagner | |
| 6,475,218 B2 | 11/2002 | Gournay et al. | |
| 6,485,491 B1 | 11/2002 | Farris et al. | |
| 6,554,831 B1 | 4/2003 | Rivard et al. | |
| 6,562,040 B1 | 5/2003 | Wagner | |
| 6,565,565 B1 | 5/2003 | Yuan et al. | |
| 6,589,243 B1 | 7/2003 | Viart et al. | |
| 6,595,992 B1 | 7/2003 | Wagner et al. | |
| 6,613,050 B1 | 9/2003 | Wagner et al. | |
| 6,626,908 B2 | 9/2003 | Cooper et al. | |
| 6,641,585 B2 | 11/2003 | Sato et al. | |
| 6,656,180 B2 | 12/2003 | Stahurski | |
| 6,740,089 B2 | 5/2004 | Haider | |
| 6,746,449 B2 | 6/2004 | Jones et al. | |
| 6,749,361 B2 | 6/2004 | Hermann et al. | |
| 6,805,716 B2 | 10/2004 | Ralph et al. | |
| 6,911,030 B1 | 6/2005 | Vanacker et al. | |
| 6,945,972 B2 | 9/2005 | Frigg et al. | |
| RE39,035 E | 3/2006 | Finn et al. | |
| 7,160,300 B2 | 1/2007 | Jackson | |
| 7,322,979 B2 | 1/2008 | Crandall et al. | |
| 7,338,490 B2 | 3/2008 | Ogilvie et al. | |
| 7,485,133 B2 | 2/2009 | Cannon et al. | |
| 7,608,095 B2 | 10/2009 | Yuan et al. | |
| 7,651,516 B2 | 1/2010 | Petit et al. | |
| 7,674,277 B2 | 3/2010 | Burd et al. | |
| 7,780,703 B2 | 8/2010 | Yuan et al. | |
| 7,785,352 B2 | 8/2010 | Snyder et al. | |
| 7,789,899 B2 | 9/2010 | Markworth et al. | |
| 7,819,901 B2 | 10/2010 | Yuan et al. | |
| 7,935,133 B2 | 5/2011 | Malek | |
| 7,988,694 B2 | 8/2011 | Barrus et al. | |
| 8,114,092 B2 | 2/2012 | Altarac et al. | |
| 8,202,299 B2 | 6/2012 | Wang et al. | |
| 8,343,163 B1 | 1/2013 | Arambula et al. | |
| 2003/0040746 A1* | 2/2003 | Mitchell | A61B 17/1606 623/17.11 |
| 2004/0111091 A1* | 6/2004 | Ogilvie | A61B 17/7056 606/276 |
| 2004/0147937 A1 | 7/2004 | Dunbar et al. | |
| 2005/0113927 A1 | 5/2005 | Malek | |
| 2005/0137593 A1 | 6/2005 | Gray et al. | |
| 2006/0084990 A1 | 4/2006 | Gournay et al. | |
| 2006/0200132 A1 | 9/2006 | Chao et al. | |
| 2006/0235426 A1 | 10/2006 | Lim et al. | |
| 2007/0016189 A1 | 1/2007 | Lake et al. | |
| 2007/0043359 A1* | 2/2007 | Altarac | A61B 17/025 606/86 A |
| 2007/0049931 A1 | 3/2007 | Justis et al. | |
| 2007/0162010 A1 | 7/2007 | Chao et al. | |
| 2007/0282337 A1 | 12/2007 | Garamszegi | |
| 2008/0228225 A1* | 9/2008 | Trautwein | A61B 17/1606 606/246 |
| 2008/0306488 A1 | 12/2008 | Altarac et al. | |
| 2009/0234395 A1 | 9/2009 | Hoffman et al. | |
| 2009/0318970 A1 | 12/2009 | Butler et al. | |
| 2010/0222822 A1 | 9/2010 | Farris et al. | |
| 2010/0274291 A1 | 10/2010 | McClellan, III et al. | |
| 2010/0305616 A1* | 12/2010 | Carbone | A61B 17/7044 606/264 |

* cited by examiner

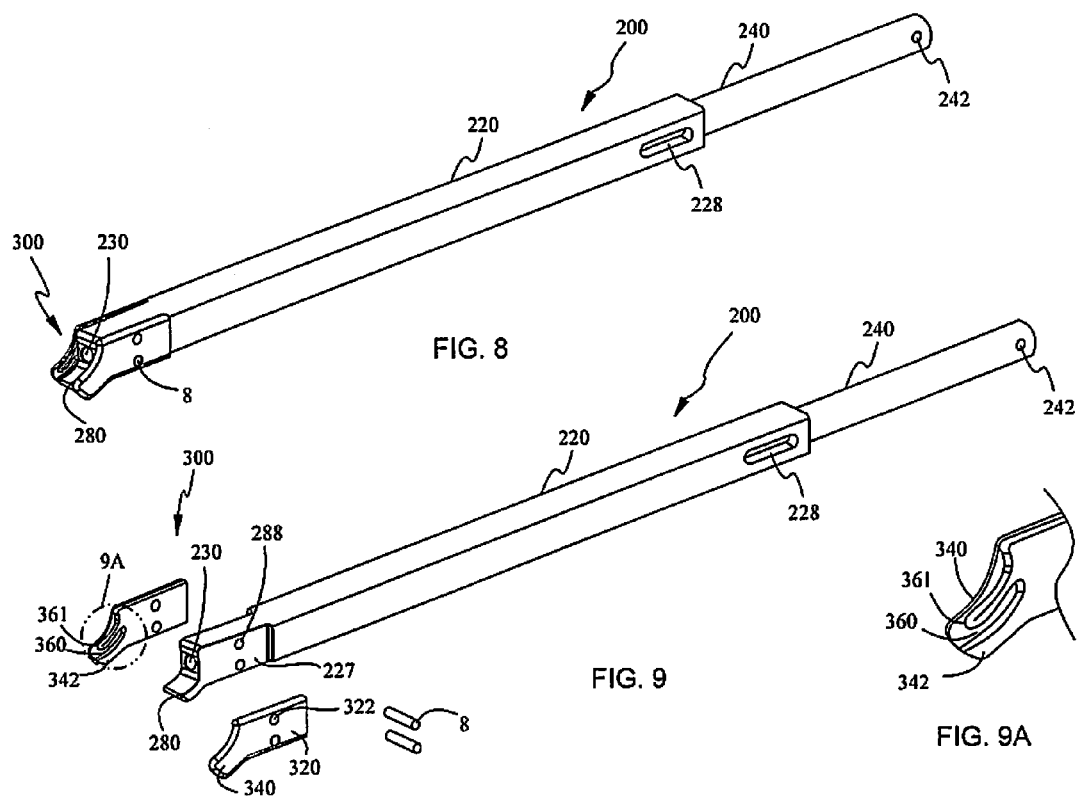

LAMINAR HOOK INSERTION DEVICE

CROSS REFERENCE TO RELATED APPLICATIONS

This application is a divisional of U.S. patent application Ser. No. 13/209,542, filed on Aug. 15, 2011, now U.S. Pat. No. 9,247,962, the entire contents of which are incorporated by reference herein.

BACKGROUND

1. Technical Field

The present disclosure relates to an orthopedic surgical device, and more particularly, to a laminar hook insertion device.

2. Background of Related Art

Spinal implant systems have been developed to achieve immobilization of vertebral bodies of the spine in a particular spatial relationship to correct spinal irregularities and to restore stability to traumatized areas of the spine. These spinal implant systems may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally by coupling to the pedicles via screws, or by means of hooks which attach under the lamina and entering into the central canal. In either case, the implants generally include elongate support rod elements which are coupled to the screws or hooks to immobilize several sequential vertebrae, for example to hold them stable so that adjacent bones may be fused with bone graft.

Such hook and rod assemblies generally include a plurality of hooks having rounded blade portions, flat extending members of which are inserted posteriorly under the lamina between the transverse process and the spinous process. The hooks further include upper body portions to which the support rod may be coupled. The rod extends along the axis of the spine, coupling to each of a plurality of hooks via receiving portions of their bodies. The aligning influence of the rod forces the spine to which it is affixed, to conform to a more proper shape.

It has been identified, however, that a considerable difficulty may be associated with inserting hooks under sequential lamina along a misaligned curvature and simultaneously precisely aligning their rod receiving portions with the rod to receive the rod therethrough without distorting, tilting, rotating, or exerting undesired translational forces on the hooks. Correction of this difficulty requires the time consuming and difficult tasks of reshaping the rods or repositioning the hooks, each of which is understood to require considerably longer operating time, which is known to increase the incidence of complications associated with surgery. Accordingly, there is a need for a device that facilitates the process of inserting hooks under sequential lamina.

SUMMARY

In accordance with an embodiment of the present disclosure, there is provided a surgical hook insertion device including an elongate body and an actuation assembly. The elongate body defines a lumen therethrough. The elongate body includes a retaining portion configured and dimensioned to releasably retain a laminar hook therein. The actuation assembly includes an actuation rod and an actuator member. The actuation rod is slidably disposed within the lumen of the elongate body. The actuator member is operatively coupled with the actuation rod and is slidably mounted on the elongate body, wherein the actuation assembly is transitionable between a first position in which a portion of the actuation rod engages the laminar hook releasably disposed in the retaining portion and a second position in which the actuation rod disengages the laminar hook.

The surgical hook insertion device may further include a biasing member, wherein the biasing member urges the actuation assembly to the first position. The elongate body may define a cavity configured and dimensioned to enable sliding movement of a pin coupling the actuation rod and the actuator member therein.

The retaining portion of the elongate body may include a seating protrusion adapted to engage and retain a hooked portion of the laminar hook. The seating protrusion may conform to the contour of the hooked portion of the laminar hook. In addition, the retaining portion may include a pair of support plates engaging lateral sides of the seating protrusion. Each of the pair of support plates may define a groove configured to retain a portion of the laminar hook therein.

The lumen defined in the elongate body may include a first portion and a second portion. The first portion of the lumen may have a larger diameter than that of the second portion. The actuation rod may include a first portion and a second portion. The first portion of the actuation rod may have a larger diameter than that of the second portion. The first and second portions of the lumen may be configured and dimensioned to receive the first and second portions of the actuation rod therein, respectively.

The surgical hook insertion device may further include a handle member defining a channel therethrough. The channel may be dimensioned to receive the first portion of the actuation rod. The actuator member may be disposed adjacent the handle member.

In accordance with another embodiment of the present disclosure, there is provided a surgical implant insertion assembly including a handle member, an elongate body, an actuation assembly, and a laminar hook. The handle member defines a channel therethrough. The elongate body defines a lumen therethrough. The elongate body is disposed at least partially within the channel of the handle assembly. The lumen is in communication with the channel. The elongate body includes a retaining portion adapted to releasably retain a laminar hook therein. The actuation assembly includes an actuation rod and an actuator member. The actuation rod is slidably disposed within the lumen of the elongate body. The actuator member is operatively coupled with the actuation rod. The actuator member is slidably mounted on the elongate body assembly. The laminar hook includes a hooked portion and a head portion. The hook portion defines a recess configured and dimensioned to releasably engage a portion of the actuation rod, wherein the actuation assembly is transitionable between a first position in which a distal portion of the actuation rod engages the laminar hook in the retaining portion and a second position in which the actuation rod disengages the laminar hook.

The surgical implant insertion assembly may further include a biasing member disposed in a proximal portion of the elongate body, wherein the biasing member urges the actuation assembly to the first position. The elongate body may define a cavity adjacent the handle member, the cavity configured and dimensioned to enable sliding movement of a pin coupling the actuation rod with the actuator member. The retaining portion of the elongate body may include a seating protrusion adapted to engage and retain a hooked portion of the laminar hook. The seating protrusion may conform to the contour of the hooked portion of the laminar hook. The retaining portion may include a pair of support plates engaging lateral sides of the seating protrusion. Each of the pair of support plates may define a groove configured to retain a portion of the laminar hook therein.

In addition the lumen defined in the elongate body may include a first portion and a second portion. The first portion of the lumen may have a larger diameter than that of the second portion. The actuation rod may include a first portion and a second portion. The first portion of the actuation rod may have a larger diameter than that of the second portion. The first and second portions of the lumen may be configured and dimensioned to receive the first and second portions of the actuation rod therein, respectively. The head portion of the laminar hook may define a bore configured and dimensioned to receive a bone screw therein.

In accordance with another aspect of the present disclosure, there is provided a method of stabilizing the spine. The method includes providing a surgical hook insertion device including an elongate body and an actuation rod. The elongate body defines a lumen therethrough. The elongate body has a retaining portion configured and dimensioned to releasably retain a laminar hook therein. The actuation rod is slidably disposed within the lumen of the elongate body, wherein the actuation rod is transitionable between a first position in which a portion of the actuation rod engages the laminar hook releasably disposed in the retaining portion and a second position in which the actuation rod disengages the laminar hook. The method further includes positioning the laminar hook to a bone, implanting a bone screw into the bone through the laminar hook, inserting a connecting rod into a connecting rod slot in the bone screw, and locking the connecting rod in the connecting rod slot in the bone screw.

The method may further include bending the connecting rod prior to inserting a connecting rod into a connecting rod slot in the bone screw. In addition, bending the connecting rod may include bending the connecting rod to conform to a desire contour of the spine.

In an embodiment, the spinal hook insertion device may further include a biasing member disposed in a proximal portion of the elongate body, wherein the biasing member urges the actuation rod to the first position. Furthermore, the spinal hook insertion device may include an actuator member operatively coupled with the actuation rod and slidably mounted on the elongate body. Moreover, the spinal hook insertion device may further include a laminar hook including an arched portion and a head portion. The arched portion may define a recess configured and dimensioned to releasably engage a portion of the actuation rod. The head portion of the laminar hook may include a threaded bore configured and dimensioned to receive therethrough the bone screw. In particular, implanting a bone screw into the bone through the laminar hook may include inserting the bone screw through the threaded bore defined in the head portion of the laminar hook. Positioning the laminar hook to a bone may include positioning the arched portion of the laminar hook on an undersurface of the lamina. Alternatively, positioning the laminar hook to a bone may include positioning the arched portion of the laminar hook around the pedicle.

BRIEF DESCRIPTION OF THE DRAWINGS

Various embodiments of the present disclosure are described hereinbelow with reference to the drawings, wherein:

FIG. 8 is a perspective view of the elongate body assembly of FIG. 6 illustrating a retaining portion thereof having support plates attached thereto;

FIG. 9 is a perspective view of the elongate body assembly of FIG. 8 illustrating the retaining portion with parts separated;

FIG. 9A is a perspective view of the area of detail indicated in FIG. 9;

DETAILED DESCRIPTION OF EMBODIMENTS

Figure 1:
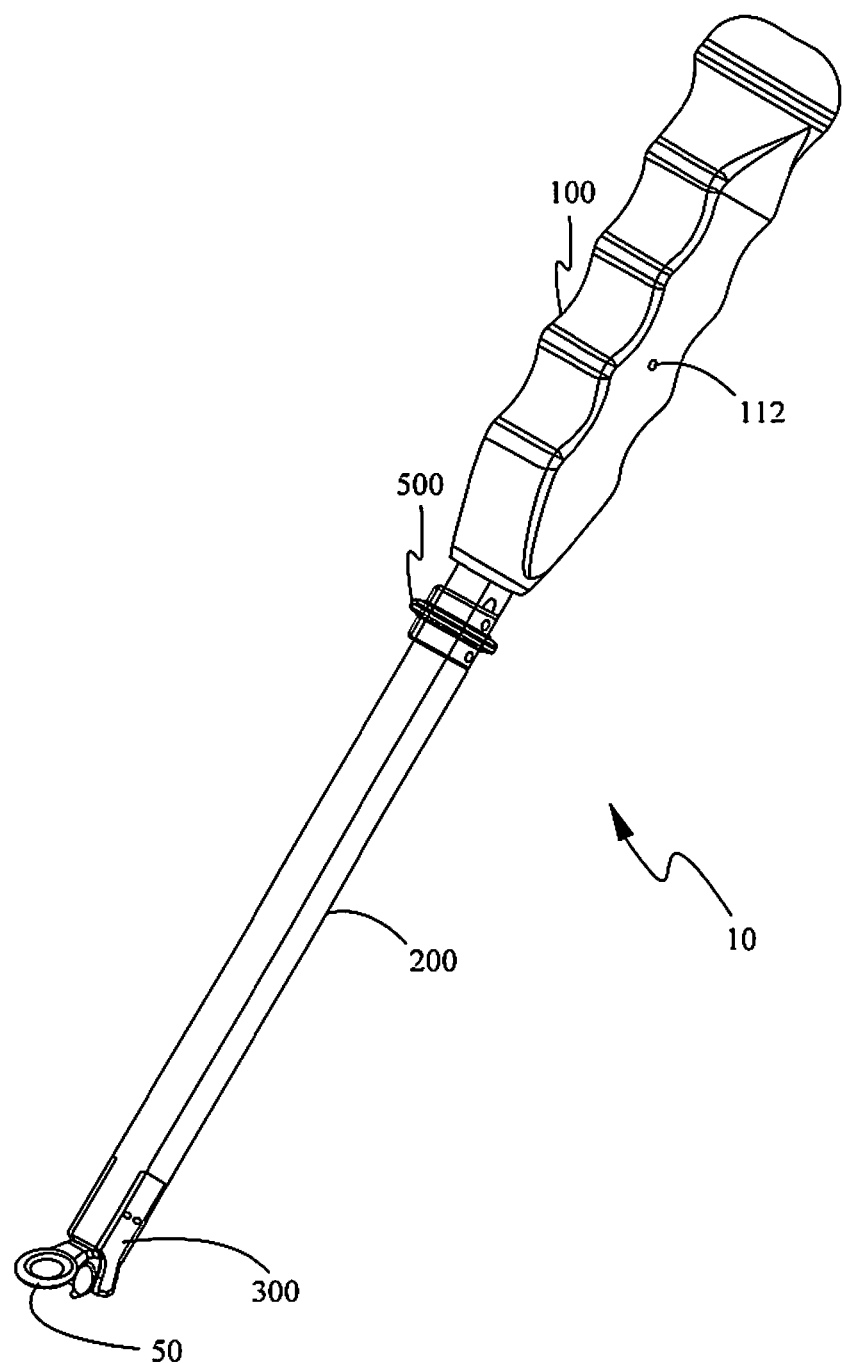
FIG. 1 is a perspective view of a laminar hook insertion device in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

Figure 2:
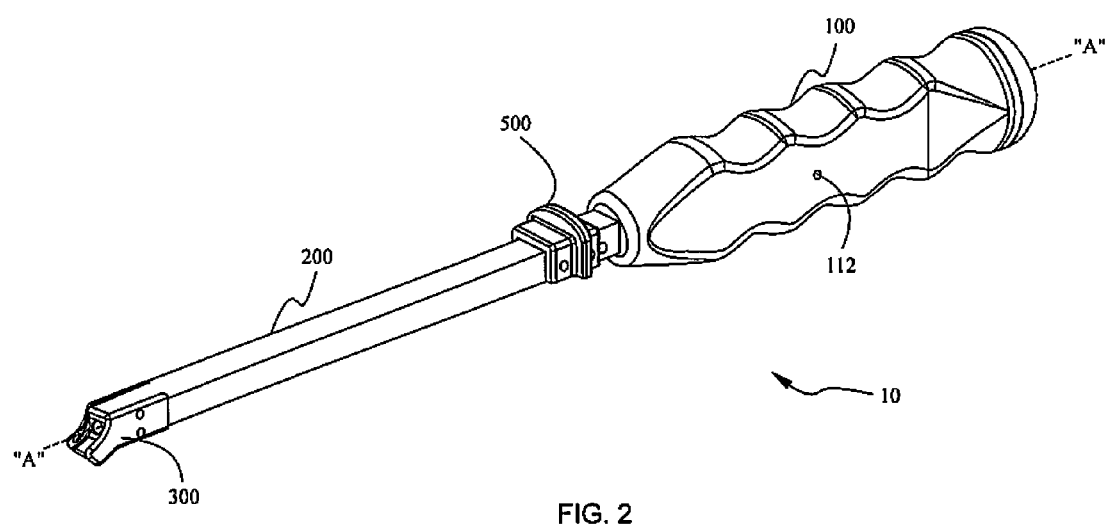
FIG. 2 is a perspective view of the laminar hook insertion device of FIG. 1 with a laminar hook removed from the insertion device.
Figure 3:
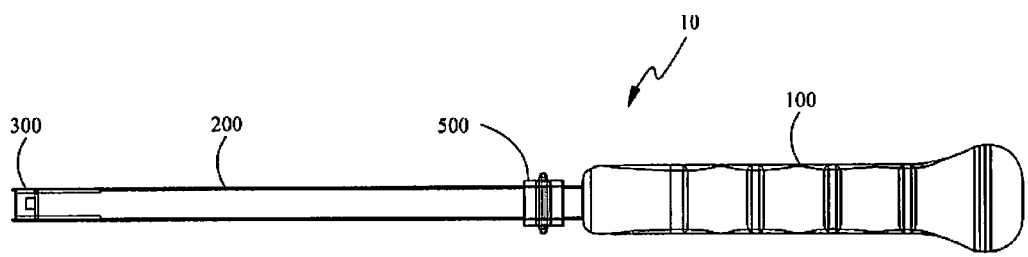
FIG. 3 is a top view of the laminar hook insertion device of FIG. 2.

With reference to FIGS. 1-3, an embodiment of the present disclosure is shown generally as a laminar hook insertion device 10 defining a longitudinal axis "A-A."

Device 10 is configured to operatively retain and release a laminar hook 50 utilized to provide coupling of a connecting rod 70 (FIG. 15) to the spine by being anchored under the lamina. Device 10 includes a handle assembly 100, an elongate body assembly 200 extending distally from handle assembly 100, a retaining portion 300 configured to releasably retain laminar hook 50 therein and an actuation assembly 500 operatively associated with laminar hook 50 for release of laminar hook 50 from an actuation rod 560 (FIG. 4) of actuation assembly 500.

Figure 14:
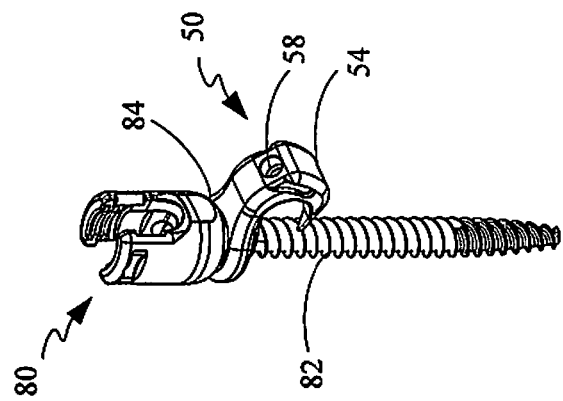
FIG. 14 is a perspective view of the laminar hook of FIG. 13 engaged with a pedicle screw.
Figure 13:
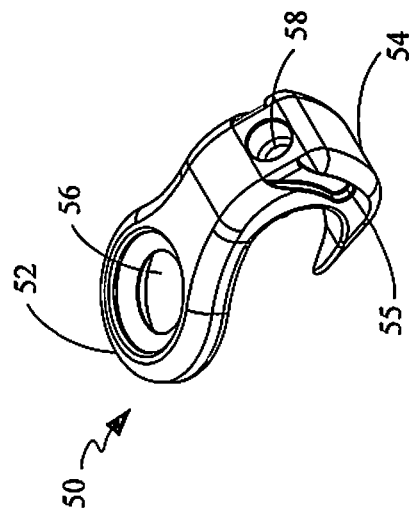
FIG. 13 is a perspective view of the laminar hook for use with the laminar hook insertion device of FIG. 1.
Figure 15:
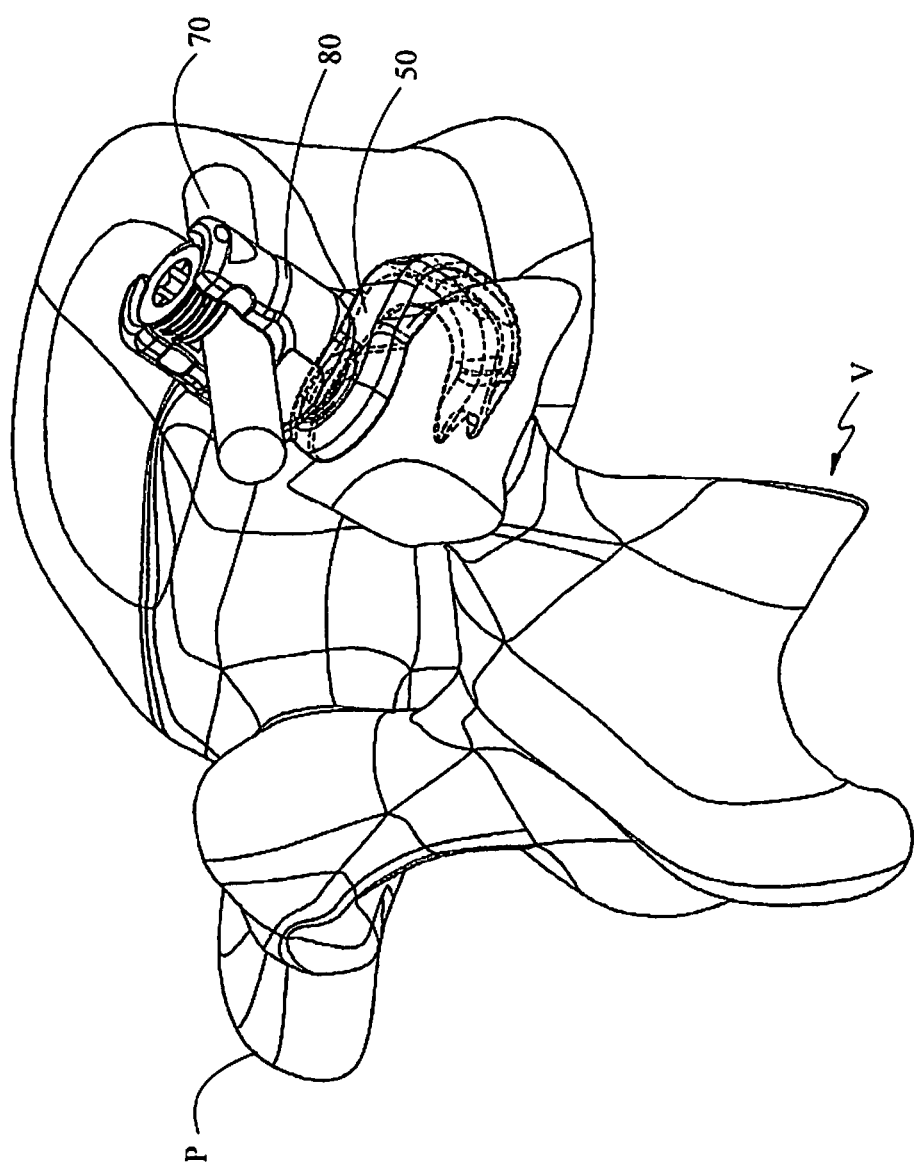
FIG. 15 is a perspective view of a vertebral body illustrating use of the laminar hook of FIG. 12 shown in phantom.

With brief reference to FIGS. 13 and 15, laminar hook 50 is configured to provide coupling of a connecting rod 70 to the spine, wherein laminar hook 50 is inserted, for example, on the undersurface of the lamina which forms a shallow arch or an inverted—V shape. In particular, laminar hook 50 includes a head portion 52 which may define a smooth bore opening 56 through which a bone screw 80 (FIG. 14) is inserted into a bone and an arched portion 54 configured to engage, for example, the undersurface of the lamina. Arched portion 54 conforms to the contour of a seating protrusion 280 (FIG. 9) of an outer body 220 to help securely retain laminar hook 50 in a retaining portion 300, as will be described hereinbelow. Moreover, arched portion 54 defines a groove 55 on each lateral side thereof and a recess 58 configured and dimensioned to securely engage a distal end portion of an actuation rod 560 (FIG. 5), as will be described hereinbelow. An example of a laminar hook is disclosed in commonly assigned U.S. patent application Ser. No. 12/812,829, filed on Aug. 18, 2010, the entire contents of which are fully incorporated herein by reference. In the alternative, it is contemplated that bore 56 may be threaded to engage threads on the bone screw or may have a lip disposed in the bore to engage threads on the screw to deform the lip and lock the screw to the hook. Such a structure is available from K2M, Inc. under the trademark tifix, substantially as described in U.S. Pat. No. 6,322,562 to Wolter.

Figure 4:
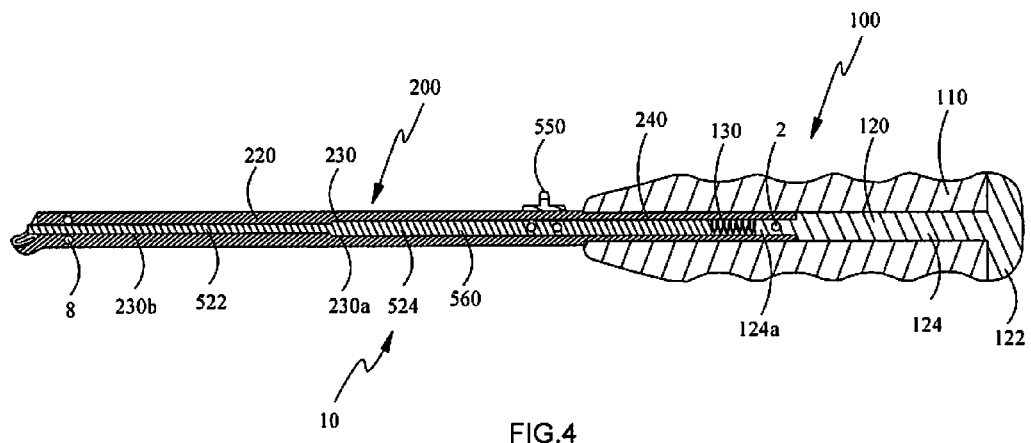
FIG. 4 is a side cross-sectional view of the laminar hook insertion device of FIG. 2.
Figure 5:
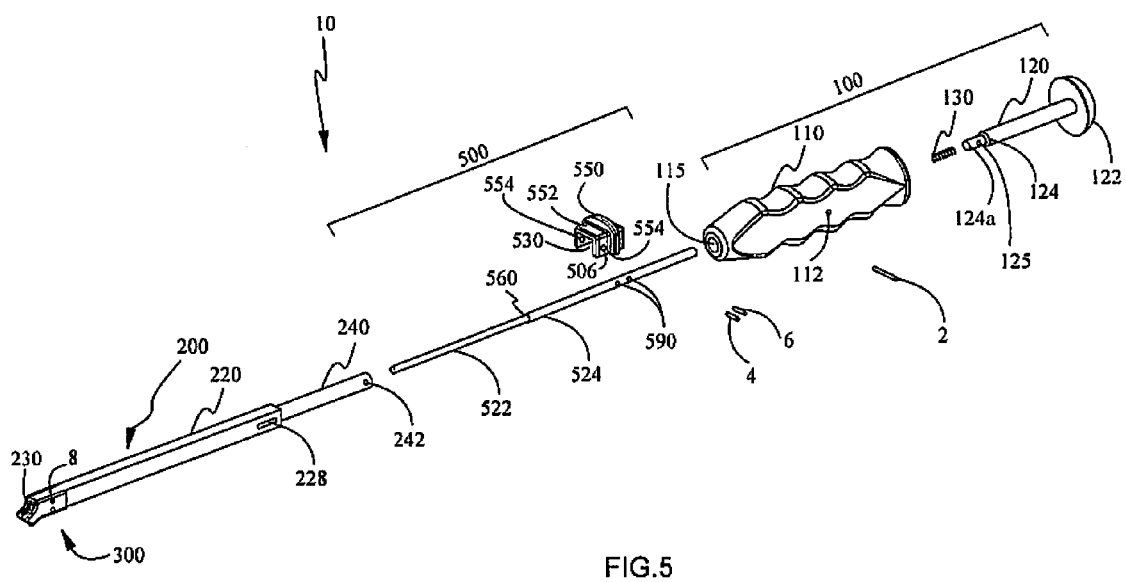
FIG. 5 is an exploded perspective view of the laminar hook insertion device of FIG. 2 with parts separated.

With reference now to FIGS. 4 and 5, handle assembly 100 includes a handle member 110 defining a channel 115 therethrough, an anchor member 120, and a biasing member 130 disposed in channel 115. In particular, anchor member 120 includes a cap 122 and a stem 124 extending distally from cap 122. Stem 124 includes a neck portion 124a disposed at a distal portion of stem 124. Neck portion 124a has a diameter smaller than that of stem 124. Neck portion 124a defines a transverse bore 125 configured to be in alignment with a lateral bore 112 defined in handle member 110. Stem 124 is configured and dimensioned to be disposed within channel 115 of handle member 110. Cap 122 engages a proximal end portion of device 10 and seals a proximal end of channel 115 of handle member 110. In addition, a pin 2 is inserted through lateral bore 112 of handle member 110 and transverse bore 125 of anchor member 120 to secure anchor member 120 with handle member 110. However, it is envisioned that handle member 110 and anchor member 120 may be detachably, e.g., threadably, coupled to each other to facilitate repair and maintenance of handle assembly 100. It is further envisioned that handle member 110 may be monolithically formed with anchor member 120.

With particular reference to FIG. 4, biasing member 130 has a diameter comparable to or smaller than that of neck portion 124a of anchor member 120. In addition, one end of biasing member 130 is positioned adjacent to a distal portion of neck portion 124a of anchor member 120. In this manner, biasing member 130 can be compressed against neck portion 124a secured with handle member 110, as will be described below.

With continued reference to FIGS. 4 and 5, elongate body assembly 200 includes an engaging member 240 and an outer body 220 extending distally from engaging member 240. Engaging member 240 is concentrically arranged with respect to outer body 220. In particular, engaging member 240 has a smaller outer diameter than that of outer body 220, such that engaging member 240 is configured and dimensioned to be disposed within at least a portion of channel 115 of handle member 110, and a proximal end portion of outer body 220 is adapted to be securely fixed to a distal end portion of handle member 110 to enclose a distal end of channel 115. In particular, a proximal end portion of engaging member 240 circumferentially surrounds neck portion 124a of anchor member 120 and provides a friction fit feature against neck portion 124a. Under such configuration, biasing member 130 is disposed in a proximal portion of engaging member 240. Engaging member 240 defines a bore 242 configured and dimensioned to receive pin 2, whereby elongate body assembly 200 is securely coupled with handle assembly 100. However, it is contemplated that engaging portion 240 of elongate body assembly 200 may be threadably connected with handle member 110.

With brief reference to FIG. 7, outer body 220 and engaging member 240 define a longitudinal lumen 230 of varying diameter, through which actuation rod 560 (FIG. 4) of actuation assembly 500 is at least partially slidably disposed, as will be described in detail hereinbelow. In particular, lumen 230 has a first portion 230a and a second portion 230b. First portion 230a of lumen 230a has a larger diameter than that of second portion 230b. The second portion 230b extends from a distal end of outer body 220 to a point along outer body 220, and first portion 230a extends from the point on outer body 220 to a proximal end of engaging member 240 configured to be disposed within a portion of channel 115 of handle member 110.

Figure 6:
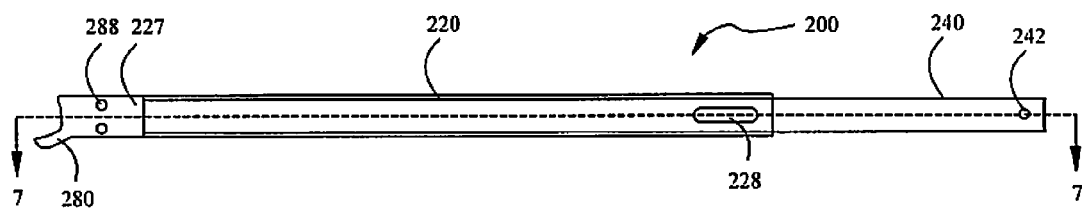
FIG. 6 is a side view of an elongate body assembly of the laminar hook insertion device of FIG. 2.
Figure 7:
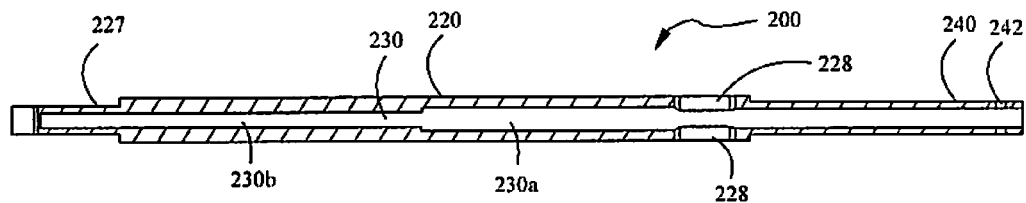
FIG. 7 is a longitudinal cross-sectional view of the elongate body assembly of FIG. 6 cut along a section line of 7-7 in FIG. 6.
Figure 10:
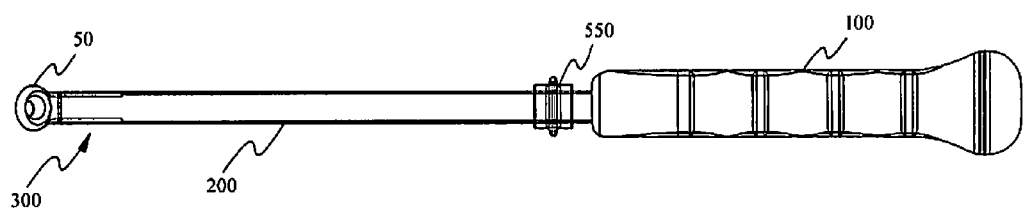
FIG. 10 is a top view of the laminar hook insertion device of FIG. 1 having a laminar hook releasably attached thereto.

With reference now to FIGS. 6 and 7, outer body 220 defines a pair of opposing cavities 228 adjacent engaging member 240 configured to be disposed within a portion of handle member 110. In particular, cavities 228 are configured and dimensioned to receive a pair of pins 4, 6 (FIG. 5) coupling actuation rod 560 with actuator member 550. Cavities 228 are configured and dimensioned to enable longitudinal movement of pins 4, 6 therein, as will be described hereinbelow.

With continued reference to FIGS. 6 and 7, the distal end portion of outer body 220 defines lateral recess portions 227. Each lateral recess portion 227 is configured and adapted to receive a support plate 320 (FIG. 9). In addition, the distal end portion of outer body 220 includes a seating protrusion 280 configured and adapted to accommodate at least a portion of laminar hook 50, as will be discussed hereinbelow.

With reference now to FIGS. 6-9, retaining portion 300 is configured to releasably retain laminar hook 50 therein. Retaining portion 300 includes a pair of support plates 320 disposed within respective lateral recess portions 227. Each support plate 320 defines a pair of bores 322 configured and dimensioned to receive pins 8 therethrough to securely engage support plate 320 with lateral recess portions 227 of outer body 220. Outer body 220 defines a pair of corresponding bores 288. In particular, the pair of bores 288 is arranged such that longitudinal movement of actuation rod 560 within lumen 230 is not affected by pins 8 therein. Specifically, pins 8 do not extend through lumen 230, and thus pins 8 are used to secure both support plates 320 to respective lateral recess portions 227.

With particular reference to FIG. 9, each support plate 320 includes a substantially flat portion that is disposed in lateral recess portion 227 of outer body 220. In addition, each support plate 320 includes a retaining member 340 that generally conforms to the contour of seating protrusion 280 of outer body 220. Moreover, retaining member 340 includes a contact surface 342 that engages a lateral surface of seating protrusion 280. Furthermore, each retaining member 340 defines a groove 360 (FIG. 9A) that is adapted to receive at least a portion of arched portion 54 of laminar hook 50 therein. Moreover, retaining member 340 includes a guide portion 361 (FIG. 9A) configured and dimensioned to engage groove 55 defined in each lateral side of arched portion 54 of laminar hook 50.

With reference back to FIGS. 4 and 5, laminar hook insertion device 10 further includes actuation assembly 500 operatively coupled with a laminar hook 50 (FIG. 11) releasably disposed in retaining portion 300. Actuation assembly 500 includes an actuation rod 560 and an actuator member 550. Actuation rod 560 includes a first portion 524 and a second portion 522 extending distally from first portion 524. First portion 524 has a larger diameter than that of second portion 522. The diameters of first and second portions 230a, 230b of lumen 230 substantially correspond to those of first and second portions 524, 522 of actuation rod 560, respectively.

With continued reference to FIG. 4, actuation rod 560 is slidably disposed in lumen 230 defined in outer body 220 and engaging member 240 of elongate body assembly 200. In particular, a proximal end portion of actuation rod 560 engages a distal end portion of biasing member 130 disposed within a proximal portion of first portion 230a of lumen 230. A distal end portion of actuation rod 560 is adapted to securely and releasably engage a recess 58 (FIG. 11) defined in laminar hook 50 disposed in retaining portion 300, whereby distal end portion of actuation rod 560 protrudes slightly through a distal end of lumen 230 of elongate body assembly 200.

With continued reference to FIGS. 4 and 5, actuator member 550 includes a base portion 552 and a pair of opposing guide members 554 extending from base member 552. Actuator member 550 defines a U-shaped cross-section defining a recess 530. Actuator member 550 is mounted on a portion of outer member 220, and is operatively coupled with actuation rod 560 disposed in lumen 230 of elongate body assembly 200. In particular, pins 4, 6 couple actuator member 550 with actuation rod 560. Specifically, pins 4, 6 are received through bores 506 defined in opposing guide members 554 and bores 590 defined in first portion 524 of actuation rod 560 through cavity 228 defined in outer body 220. In this manner, actuator member 550 mounted on at least a portion of outer body 220 is slidable along cavity 228 of outer body 220, which in turn imparts longitudinal movement to actuation rod 560 slidably disposed within lumen 230 defined in elongate body assembly 200.

However, movement of actuation rod 560 is limited by biasing member 130 in the proximal direction and by second portion 230b of lumen 230 which defines a smaller diameter than that of first portion of 524 of actuation rod 560 in the distal direction. Accordingly, when biasing member 130 is in a neutral state, i.e., unactuated state (FIG. 11), biasing member 130 urges actuation rod 560 to the distal-most position within lumen 230. Specifically, a distal end portion of first portion 524 of actuation rod 560 engages a proximal end portion of second portion 230b of lumen 230, whereby the smaller diameter of second portion 230b of lumen 230 inhibits distal movement of first portion 524 of actuation rod 560 therethrough. More importantly, at this time, the distal end portion of second portion 522 of actuation rod 560 slightly extends out of the distal end of lumen 230, whereby recess 58 of laminar hook 50 is securely engaged with a distal end portion of actuation rod 560 in retaining portion 300. In addition, the distal and proximal limits of actuation rod 560 is further defined by cavity 228 defined in outer member 220 of elongate body portion 200, in which pins 4, 6 slidably move therein.

Figure 11:
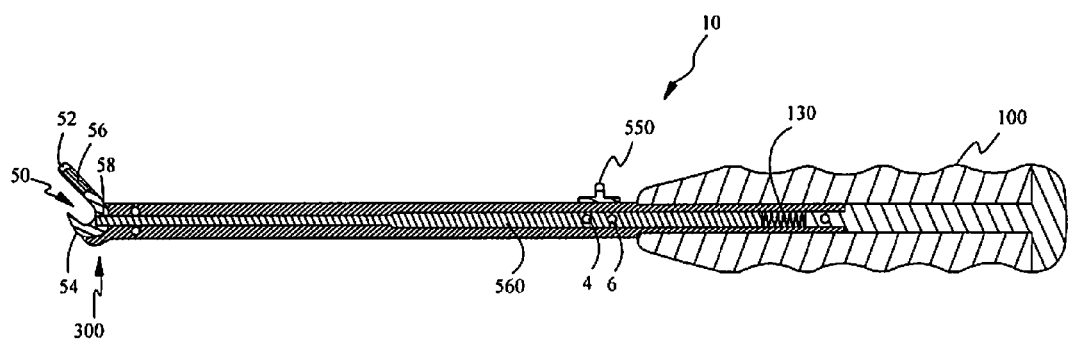
FIG. 11 is a side cross-sectional view of the laminar hook insertion device of FIG. 10.
Figure 12:
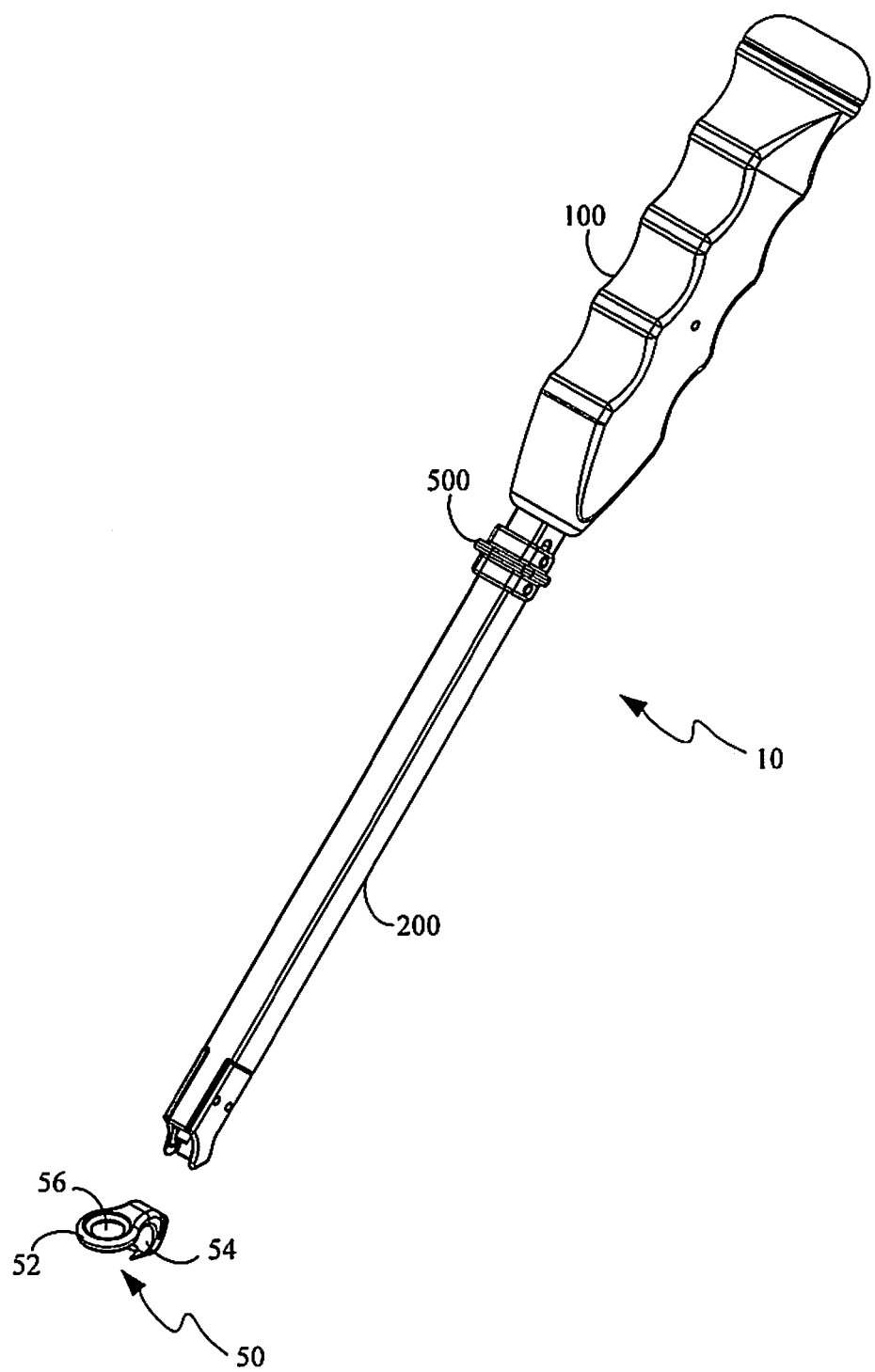
FIG. 12 is a perspective view of the laminar hook insertion device of FIG. 1 illustrating detachment of the laminar hook.

With reference to FIG. 11, when biasing member 130 is in the neutral state, a distal end portion of actuation rod 560 protrudes slightly through the distal end of lumen 230 of outer member 220 and releasably engages recess 58 of laminar hook 50. Arched portion 54 of hook 50 conforms to the contour of seating protrusion 280 (FIG. 9) of an outer body 220 to help securely retain laminar hook 50 in retaining portion 300. At this time, pin 4 connected to actuator member 550 is disposed in the distal-most position in cavity 228 defined in outer body 220 (FIG. 12). However, as actuator member 550 is slidably moved in the proximal direction by the surgeon, actuation rod 560 is also moved proximally as a single construct with actuator member 550 against the bias of biasing member 130. Such movement disengages the distal end portion of actuation rod 560 from recess 58 of laminar hook 50. Upon release of actuator member 550, the bias of biasing member 130 urges actuation rod 560 to the distal-most position, which in turn positions pin 4 connected to actuator member 550 to the distal-most position in cavity 228 defined in outer body 220.

Prior to the surgical procedure, laminar hook 50 is attached to retaining portion 300 of laminar hook insertion device 10 by sliding actuator member 550 in the proximal direction which in turn moves actuation rod 560 proximally to facilitate positioning of laminar hook 50 in retaining portion 300. Upon positioning laminar hook 50 in retaining portion 300, actuator member 560 is released to urge actuation rod 560 in the distal direction, whereby the distal portion of actuation rod 560 engages recess 58 defined in arched portion 54 of laminar hook 50. The secure attachment of laminar hook 50 to laminar hook insertion device 10 enables the surgeon to safely manipulate and deliver laminar hook 50 to the surgical site of interest.

In use, the surgeon accesses the patient's spine in a known manner either using open surgical techniques or minimally invasive techniques, and prepares the bone to receive screws, as is deemed appropriate under the circumstances. The surgeon can position arched portion 54 of laminar hook 50 to engage, for example, the undersurface of the lamina, and insert a bone screw into the bone through threaded bore 56 of laminar hook 50. For example, the bone screw may be a pedicle screw 80 (FIG. 14) including a shank 82 and a collet 84. Pedicle screw 80 may be of a rigid, unitary design or may be polyaxial. Examples of polyaxial screws are found in U.S. Pat. Nos. 5,733,286; 5,683,392 and 6,451,021, the entire contents of which are incorporated herein by reference. Collet 80 is configured and dimensioned to receive a head of shank 82 such that collet 80 and the head are rotatable and pivotable in relation to each other, thereby allowing shank 82 to be repositioned in a plurality of orientations relative to collet 80.

Alternatively, the bone screw may be a multi-planar taper lock screw (not shown) that enables manipulation of a screw shaft about multiple axes, whereby the bone screw is capable of securing connecting rod 70 with bone screws on multiple vertebral bodies that are aligned in the spinal column on different planes due to the curvature of the spine. However, it is also envisioned that the bone screws may be, for example, uniplanar screws and monoaxial taper lock screws.

Multi-planar taper lock bone screw includes a dual layered housing and screw shaft having a spherically configured screw head rotatably coupled with the housing. In particular, the dual layered housing includes an outer housing and an inner housing. The outer housing can be selectively positioned relative to the inner housing to fully lock the screw head and connecting rod 70 in position within the inner housing or alternatively to selectively partially lock the screw head and/or connecting rod 70 in position while permitting a sliding and/or rotating motion of connecting rod 70 and the screw head, respectively, relative to the bone screw.

Specifically, the outer housing is configured such that at least a portion of an inner surface of the outer housing is capable of sliding over a portion of an outer surface of the inner housing in upward and downward directions along the longitudinal axis of the bone screw. When the outer housing is slid upward in relation to the inner housing an inner surface of the outer housing causes the inner housing to impart compressive force radially inward to secure connecting rod 70 at least partially disposed therein. One suitable taper lock screw is commercially available from K2M, Inc. (Leesburg, Va.) under the trade name MESA™. In addition, suitable multi-planar taper lock screws are shown and described in U.S. Patent Application Publication 2008/0027432 and in U.S. Patent Application Publication 2007/0093817, both of which are herein incorporated by reference in their entireties. A screw head having a rod receiving notch is disclosed in commonly assigned U.S. patent application Ser. Nos. 11/493,524 and 11/493,625, the complete disclosures of which are fully incorporated herein by reference. An example of a rod reducer is disclosed in commonly assigned U.S. Pat. No. 7,771,430, the entire contents of which are fully incorporated herein by reference.

Thereafter, the surgeon reduces connecting rod 70 into the rod receiving notch of the screw head. The surgeon then uses the locking instrument to lock or partially lock each screw to rod 70. Advantageously, the surgeon may partially lock each screw and before finishing the locking step may readjust the arrangement of the screws and rods 70. Upon completion of necessary adjustments, the surgeon can then fully lock each screw with the locking instrument.

Although the illustrative embodiments of the present disclosure have been described herein with reference to the accompanying drawings, the above description, disclosure, and figures should not be construed as limiting, but merely as exemplifications of particular embodiments. For example, laminar hook 50 may be utilized to extend around the pedicle "P" in the region of the inferior vertebral notch to provide enhanced stability and fixation of the pedicle screw, as shown in FIG. 15. It is to be understood, therefore, that the disclosure is not limited to those precise embodiments, and that various other changes and modifications may be effected therein by one skilled in the art without departing from the scope or spirit of the disclosure.

What is claimed is:

1. A method of stabilizing a spine comprising:
positioning a laminar hook on a retaining portion of a surgical hook insertion device by linearly inserting a guide protrusion of the retaining portion into a groove defined in the laminar hook, such that an acute angle defined by a guide protrusion axis of the guide protrusion and a longitudinal axis defined by the surgical hook insertion device is a fixed angle while the laminar hook is slidably released along an axis from the hook retaining portion;
releasably securing the laminar hook on the retaining portion of the surgical hook insertion device by transitioning an actuation rod along the longitudinal axis of the surgical hook insertion device from a first position in which the actuation rod is disengaged from the laminar hook to a second position in which a portion of the actuation rod is engaged with the laminar hook;
positioning the laminar hook adjacent a bone of the spine;
implanting a bone screw into the bone through the laminar hook;
inserting a connecting rod into a connecting rod slot in the bone screw; and
locking the connecting rod in the connecting rod slot in the bone screw.

2. The method according to claim 1, further comprising bending the connecting rod prior to inserting the connecting rod into the connecting rod slot in the bone screw.

3. The method according to claim 2, wherein bending the connecting rod includes bending the connecting rod to conform to a desired contour of the spine.

4. The method according to claim 1, wherein releasably securing the laminar hook on the retaining portion of the surgical hook insertion device includes transitioning the actuation rod from the first position in which the portion of the actuation rod is disengaged from a recess defined in an arched portion of the laminar hook to the second position in which the actuation rod is engaged with the recess of the arched portion of the laminar hook.

5. The method according to claim 4, wherein positioning the laminar hook adjacent the bone includes positioning the arched portion of the laminar hook on an undersurface of a lamina of the spine.

6. The method according to claim 4, wherein positioning the laminar hook adjacent the bone includes positioning the arched portion of the laminar hook around a pedicle of the spine.

7. The method according to claim 1, wherein implanting the bone screw to the bone through the laminar hook includes inserting the bone screw through a threaded bore defined in a head portion of the laminar hook.

8. The method according to claim 1, wherein the longitudinal axis defined by the surgical hook insertion device is a central longitudinal axis extending between proximal and distal ends of the surgical hook insertion device.

9. A method of stabilizing a spine comprising:
positioning a laminar hook on a retaining portion of a surgical hook insertion device by linearly inserting a guide protrusion of the retaining portion into a groove defined in the laminar hook, such that the guide protrusion is rotationally fixed with respect to a central longitudinal axis of the surgical hook insertion device while the laminar hook is translatably released from the hook retaining portion of the surgical hook insertion device;
securing the laminar hook on the retaining portion of the surgical hook insertion device by transitioning an actuation rod along the central longitudinal axis of the surgical hook insertion device from a first position in which the actuation rod is disengaged from the laminar hook and a second position in which a portion of the actuation rod is engaged with the laminar hook;
positioning the laminar hook on a bone of the spine;
securing a bone screw to the bone through the laminar hook;

inserting a connecting rod into a connecting rod slot in the bone screw; and locking the connecting rod in the connecting rod slot in the bone screw.

10. The method according to claim 9, further comprising bending the connecting rod prior to inserting the connecting rod into the connecting rod slot in the bone screw.

11. The method according to claim 9, wherein bending the connecting rod includes bending the connecting rod to conform to a desired contour of the spine.

12. The method according to claim 9, wherein securing the laminar hook on the retaining portion of the surgical hook insertion device includes transitioning the actuation rod from the first position in which the portion of the actuation rod is disengaged from a recess defined in an arched portion of the laminar hook to the second position in which the actuation rod is engaged with the recess of the arched portion of the laminar hook.

13. The method according to claim 12, wherein positioning the laminar hook adjacent the bone includes positioning the arched portion of the laminar hook on an undersurface of a lamina of the spine.

14. The method according to claim 12, wherein positioning the laminar hook adjacent the bone includes positioning the arched portion of the laminar hook around a pedicle of the spine.

15. The method according to claim 9, wherein securing the bone screw to the bone through the laminar hook includes inserting the bone screw through a threaded bore defined in a head portion of the laminar hook.

\* \* \* \* \*